United States Patent [19]

Wollweber et al.

[11] 4,064,270

[45] Dec. 20, 1977

[54] N'-(AMINOACYLAMINOPHENYL) ACETAMIDINES

[75] Inventors: Hartmund Wollweber; Ekkehard Niemers; Hans Peter Schulz; Herbert Thomas; Peter Andrews, all of Wuppertal, Germany

[73] Assignee: Bayer Aktiengesellschaft, Germany

[21] Appl. No.: 505,745

[22] Filed: Sept. 13, 1974

[30] Foreign Application Priority Data

Sept. 18, 1973 Germany ............................ 2346937

[51] Int. Cl.² .......................................... C07D 295/00
[52] U.S. Cl. .................................... 424/324; 560/32; 560/163; 260/239 BF; 260/519; 260/518 A; 260/268 R; 260/293.76; 260/294.9; 260/295 R; 260/326.15; 260/326.2; 260/326.4; 260/326.47; 260/347.2; 260/347.3; 260/346.73; 260/463; 260/518 R; 260/558 A; 260/561 S; 260/562 N; 544/165; 544/159; 544/163; 544/143; 548/336; 548/342

[58] Field of Search .................... 260/562 N; 424/324

[56] References Cited

U.S. PATENT DOCUMENTS 3,336,384 8/1967 Gee .................................. 260/562 N
3,729,470 4/1973 Vaille .............................. 260/562 N Primary Examiner—Paul J. Killos
Attorney, Agent, or Firm—Jacobs & Jacobs

[57] ABSTRACT

A new class of N'-(aminoacylaminophenyl) acetamidines:

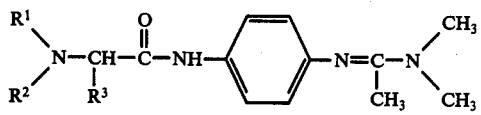

in which $R^1$ and $R^2$ are the same or different and represent hydrogen, alkyl, aryl or the substituted derivatives thereof or, together with the nitrogen atom to which they are attached, an heterocyclic ring; and $R^3$ is hydrogen, alkyl, aryl, aralkyl, or a heterocyclic moiety including the substituted derivatives thereof. The products have utility as anthelmintics.

The products are obtained by treating a suitable amino-acid or a carbonyl-activated amino-acid, with the appropriate N'-(4-aminophenyl)-N,N-dimethylacetamidine. In addition, the products are obtained by treating a suitable N'-(haloacylaminophenylacetamidine with an appropriate amine.

63 Claims, No Drawings

N'-(AMINOACYLAMINOPHENYL) ACETAMIDINES

This invention relates to a new class of N'-(aminoacylaminophenyl)acetamidine compounds and to a method for their preparation. The products exhibit pharmacological activity and are especially useful as anthelmintics.

It is known from German Published Specification No. 2,029,298 and German Published Specification No. 2,029,299 that N'-phenyl-N,N-dimethylacetamidines are active against helminths. However, these compounds exhibit a relatively low therapeutic index.

This invention provides compounds which are N'-(aminoacylaminophenyl)acetamidines of the following general formula and the non-toxic pharmacologically acceptable salts thereof:

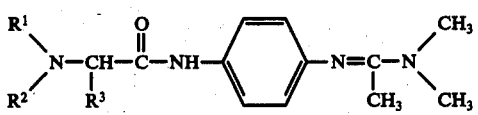

wherein $R^1$ and $R^2$ are the same or different and represent hydrogen; alkyl unsubstituted or substituted by one, two or three of the same or different members selected from the group consisting of alkoxy, alkylthio, haloalkyl, hydroxy, halo, cyano, nitro, amino, monoalkylamino, dialkylamino, carboxy, carbalkoxy, sulfo, alkylsulfonyl and arylsulfonyl; or aryl unsubstituted or substituted by one, two or three of the same or different members selected from the group consisting of alkoxy, alkylthio, haloalkyl, hydroxy, halo, cyano, nitro, amino, monoalkylamino, dialkylamino, carboxy, carbalkoxy, sulfo, alkylsulfonyl and arylsulfonyl; or $R^1$ and $R^2$, taken together with the nitrogen atom to which they are attached, represent a saturated or unsaturated 5- to 7-membered heterocycle or a 5- to 7-membered heterocycle in which the nucleus may contain one further oxy, thio, nitrogen, thiodioxide, imino or N-alkylimino moiety;

$R^3$ is hydrogen, alkyl unsubstituted or substituted by one, two or three of the same or different members selected from the group consisting of alkoxy, amido, mercapto, alkylthio, haloalkyl, hydroxy, halo, cyano, nitro, amino, monoalkylamino, dialkylamino, carboxy, carbalkoxy, sulfo, alkylsulfonyl, arylsulfonyl and 2-indolyl; 3-indolyl, 4-imidazolyl, 2-pyridyl, 3-pyridyl, 4-pyridyl, 2-furyl, 2-tetrahydrofuryl; aryl unsubstituted or substituted by one, two or three of the same or different members selected from the group consisting of alkoxy, alkylthio, haloalkyl, hydroxy, halo, cyano, nitro, amino, monoalkylamino, dialkylamino, carboxy, carbalkoxy, sulfo, alkylsulfonyl and arylsulfonyl; aralkyl unsubstituted or substituted by one, two or three of the same or different members selected from the group consisting of alkoxy, alkylthio, haloalkyl, hydroxy, halo, cyano, nitro, amino monoalkylamino, dialkylamino, carboxy, carbalkoxy, sulfo, alkylsulfonyl and arylsulfonyl; a heterocycle selected from the group consisting of indole, imidazole, pyridine, pyrimidine, thiophene, furan and tetrahydrofuran or $R^2$ and $R^3$, taken together with the nitrogen and carbon to which they are attached, represent 2-pyrrolidyl.

Typical of the alkyl radicals within the definition of $R^1$, $R^2$ and $R^3$ in formula (I) are the straight or branched chain alkyl of 1 to 6 carbon atoms and, preferably, 1 to 4 carbon atoms as, for example, methyl, ethyl, n- and i-propyl, n-butyl, iso-butyl and tert.-butyl.

Aryl radicals within the definition of $R^1$, $R^2$ and $R^3$ are those of 6 to 10 nuclear carbon atoms in the aromatic nucleus as, for example, phenyl and naphthyl.

Aralkyl radicals within the definition of $R^3$ are aralkyl radicals optionally substituted in the aryl and/or alkyl portion of the molecule and preferably having 6 to 10 nuclear carbon atoms but especially phenylalkyl containing 1 to 4 carbon atoms or, preferably, 1 or 2 carbon atoms in the straight or branched chain alkyl moiety. Illustrative of these radicals are, for example, benzyl and phenethyl.

$R^1$ and $R^2$, taken together with the nitrogen atom to which they are attached, represent a saturated or unsaturated 5- to 7-membered heterocyclic ring or a 5- to 7-membered heterocyclic ring which may contain as an additional hetero-atom from 1 to 3 but, preferably 1, oxy, thio, nitrogen, thiodioxide, imino or N-alkylimino moiety; the said nitrogen and sulphur atoms are preferably an —$SO_2$— or —N(alkyl)-moiety, with "alkyl" in the said —N(alkyl)-moiety preferably containing 1 to 4 and, preferably, 1 to 2 carbon atoms. Methyl, ethyl, n- and i-propyl and n-, i- and t.-butyl radicals may be mentioned as examples of suitable alkyl radicals. The heterocyclic ring itself generally contains 5 to 7, preferably 5 or 6, ring members. The 6-membered heterocyclic ring preferably contains the hetero-atom of the heterogroup in the para-position to the amine nitrogen atom. Pyrrolidine, piperidine, piperazine, hexamethyleneimine, morpholine and N-methylpiperazine rings may be mentioned as preferred examples of the heterocyclic ring.

The alkyl and aryl radicals within the definition of $R^1$, $R^2$ and $R^3$ include the substituted derivatives thereof as, for example, those containing 1 or more but, preferably, 1 to 3 and, most preferably, 1 or 2 identical or different substituents. The following are illustrative of these substituents: alkyl with, preferably, 1 to 4 but especially 1 or 2 carbon atoms, such as methyl, ethyl, n- and i-propyl and n-, i- and t-butyl; alkoxy with, preferably, 1 to 4 but especially 1 or 2 carbon atoms, such as methoxy, ethoxy, n- and i-propoxy and n-, i- and t.-butoxy; alkylthio with, preferably 1 to 4 but especially 1 or 2 carbon atoms, such as methylthio, ethylthio, n- and i-propylthio and n-, i- and t.-butylthio; haloalkyl with, preferably, 1 to 4 but especially 1 or 2 carbon atoms and with 1 to 5 but especially 1 to 3 halo moieties, the halo moieties being identical or different and, preferably, fluoro, chloro or bromo, especially fluoro, with the preferred haloalkyl being trifluoromethyl; hydroxy; halo, preferably fluoro, chloro, bromo and iodo but especially chloro and bromo; cyano; nitro; amino; monoalkylamino and dialkylamino of 1 to 4 but especially 1 or 2 carbon atoms per alkyl, such as methylamino, methylethylamino, n- and i-propylamino and methyl-n-butylamino; carboxy; carbalkoxy with, preferably 2 to 4 but especially 2 or 3 carbon atoms such as carbomethoxy and carboethoxy; sulfo (—$SO_3H$); alkylsulfonyl with, preferably, 1 to 4 but especially 1 or 2 carbon atoms such as methylsulfonyl and ethylsulfonyl and arylsulfonyl with, preferably, 6 or 10 nuclear carbon atoms such as phenylsulfonyl and naphthylsulfonyl.

One embodiment of this invention covers the following N'-(aminoacylaminophenyl)acetamidines:

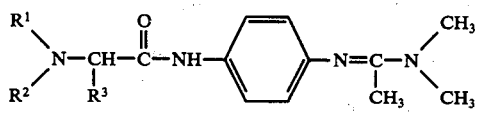

wherein $R^1$ and $R^2$ are the same or different and represent hydrogen, alkyl of 1 to 6 carbon atoms unsubstituted or substituted by one, two or three of the same or different members selected from the group consisting of alkoxy of 1 to 4 carbon atoms, alkylthio of 1 to 4 carbon atoms, haloalkyl of 1 to 4 carbon atoms and 1 to 5 halo moieties, hydroxy, halo, cyano, nitro, amino, monoalkylamino of 1 to 4 carbon atoms, dialkylamino in which each alkyl moiety contains from 1 to 4 carbon atoms, carboxy, carbalkoxy of 2 to 4 carbon atoms, sulfo, alkylsulfonyl of 1 to 4 carbon atoms and arylsulfonyl of 6 to 10 carbon atoms; or aryl of 6 to 10 carbon atoms unsubstituted or substituted by one, two or three of the same or different members selected from the group consisting of alkoxy of 1 to 4 carbon atoms, alkylthio of 1 to 4 carbon atoms, haloalkyl of 1 to 4 carbon atoms and 1 to 5 halo moieties, hydroxy, halo, cyano, nitro, amino, monoalkylamino of 1 to 4 carbon atoms, dialkylamino in which each alkyl moiety contains from 1 to 4 carbon atoms, carboxy, carbalkoxy of 2 to 4 carbon atoms, sulfo, alkylsulfonyl of 1 to 4 carbon atoms and arylsulfonyl of 6 to 10 carbon atoms; or $R^1$ and $R^2$, taken together with the nitrogen atom to which they are attached, represent a 5- to 7-membered heterocycle in which nitrogen is the single hetero atom or which, in addition to the said nitrogen atom, contains one additional hetero atom selected from the group consisting of oxy, thio, thiodioxide, imino and N-alkylimino;

$R^3$ is hydrogen, alkyl of 1 to 6 carbon atoms unsubstituted or substituted by one, two or three of the same or different members selected from the group consisting of alkoxy of 1 to 4 carbon atoms, amido, mercapto, alkylthio of 1 to 4 carbon atoms, haloalkyl of 1 to 4 carbon atoms and 1 to 5 halo moieties, hydroxy, halo, cyano, nitro, amino, monoalkylamino of 1 to 4 carbon atoms, dialkylamino in which each alkyl moiety contains from 1 to 4 carbon atoms, carboxy, carbalkoxy of 2 to 4 carbon atoms, sulfo, alkylsulfonyl of 1 to 4 carbon atoms, arylsulfonyl of 6 to 10 carbon atoms and 2-indolyl; or an heterocycle selected from the group consisting of indole, imidazole, furan and tetrahydrofuran, or $R^2$ and $R^3$, taken together with the nitrogen and carbon to which they are attached, represent 2-pyrrolidyl;

and the non-toxic pharmacologically acceptable salts thereof.

Another embodiment of this invention relates to N'-(aminoacylaminophenyl)acetamidines of the following structure and scope:

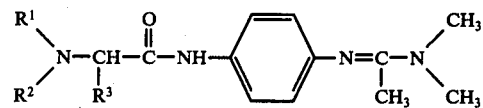

wherein $R^1$ and $R^2$ are the same or different and represent hydrogen; alkyl of 1 to 4 carbon atoms unsubstituted or substituted by one, two or three of the same or different members selected from the group consisting of alkoxy of 1 or 2 carbon atoms, alkylthio of 1 or 2 carbon atoms, haloalkyl of 1 or 2 carbon atoms and 1 to 3 halo moieties, hydroxy, halo, cyano, nitro, amino, monoalkylamino of 1 or 2 carbon atoms, dialkylamino in which each alkyl contains 1 or 2 carbon atoms, carboxy, carbalkoxy of 2 or 3 carbon atoms, sulfo, alkylsulfonyl of 1 or 2 carbon atoms and phenylsulfonyl; phenyl, naphthyl, substituted phenyl or substituted naphthyl in which the substituents on the phenyl and naphthyl nuclei are one, two or three of the same or different members selected from the group consisting of alkoxy of 1 or 2 carbon atoms, alkylthio of 1 or 2 carbon atoms, haloalkyl of 1 or 2 carbon atoms and 1 to 3 halo moieties, hydroxy, halo, cyano, nitro, amino, monoalkylamino of 1 or 2 carbon atoms, dialkylamino in which each alkyl contains from 1 or 2 carbon atoms, carboxy, carbalkoxy of 2 or 3 carbon atoms, sulfo, alkylsulfonyl of 1 or 2 carbon atoms and phenylsulfonyl; or $R^1$ and $R^2$, taken together with the nitrogen atom to which they are attached, represent pyrrolidino, piperidino, piperazino, hexamethyleneimino, morpholino or N-methylpiperazino;

$R^3$ is hydrogen, alkyl of 1 to 2 carbon atoms unsubstituted or substituted by one, two or three of the same or different members selected from the group consisting of alkoxy of 1 or 2 carbon atoms, amido, mercapto, alkylthio of 1 or 2 carbon atoms, haloalkyl of 1 or 2 carbon atoms and 1 to 3 halo moieties, hydroxy, halo, cyano, nitro, amino, monoalkylamino of 1 or 2 carbon atoms, dialkylamino in which each alkyl contains from 1 or 2 carbon atoms, carboxy, carbalkoxy of 2 or 3 carbon atoms, sulfo, alkylsulfonyl of 1 or 2 carbon atoms, phenylsulfonyl and 2-indolyl, 3-indolyl, 4-imidazolyl, 2-pyridyl, 3-pyridyl, 4-pyridyl, 2-furyl, 2-tetrahydrofuryl; phenyl, naphthyl, phenyl substituted by one, two or three of the same or different members selected from the group consisting of alkoxy, alkylthio, haloalkyl, hydroxy, halo, cyano, nitro, amino, monoalkylamino, dialkylamino, carboxy, carbalkoxy, sulfo, alkylsulfonyl; and arylsulfonyl phenylalkyl containing 1 or 2 carbon atoms in the straight or branched chain alkyl moiety or nuclear substituted phenylalkyl of 1 or 2 carbon atoms in the straight or branched chain alkyl moiety wherein the substituents are one, two or three of the same or different members selected from the group consisting of alkoxy of 1 or 2 carbon atoms, alkylthio of 1 or 2 carbon atoms, haloalkyl of 1 or 2 carbon atoms and 1 to 3 halo moieties, hydroxy, halo, cyano, nitro, amino, monoalkylamino of 1 or 2 carbon atoms, dialkylamino in which each alkyl contains from 1 or 2 carbon atoms, carboxy, carbalkoxy of 2 or 3 carbon atoms, sulfo, alkylsulfonyl of 1 or 2 carbon atoms and phenylsulfonyl; or an heterocycle selected from the group consisting of indole, imidazole, pyridine, pyrimidine, thiophene, furan and tetrahydrofuran or $R^2$ and $R^3$, taken together with the nitrogen and carbon to which they are attached, represent 2-pyrrolidyl;

and the non-toxic pharmacologically acceptable salts thereof.

Still another embodiment of this invention relates to the following compounds:

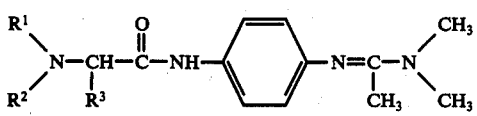

wherein $R^1$ and $R^2$ are the same or different and represent hydrogen; alkyl of 1 to 5 carbon atoms or, taken together with the nitrogen atom to which they are attached, piperidino or morpholino;

$R^3$ is hydrogen, alkyl of 1 to 5 carbon atoms, monosubstituted alkyl wherein the substituent is amino, carboxy, amido, mercapto, hydroxy, alkylthio of 1 or 2 carbon atoms of 2-indyl; phenyl, phenylalkyl containing 1 or 2 carbon atoms in the alkyl chain or nuclear hydroxy substituted phenylalkyl containing 1 or 2 carbon atoms in the alkyl chain; or $R^2$ and $R^3$, taken together with the nitrogen and carbon to which they are attached, represent 2-pyrrolidyl;

and the non-toxic pharmacologically acceptable salts thereof.

A further embodiment of this invention relates to the following compounds:

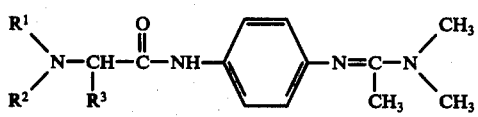

wherein $R^1$ and $R^2$ are the same or different and represent hydrogen, methyl, ethyl, n-butyl or, taken together with the nitrogen atom to which they are attached, piperazino or morpholino;

$R^3$ is hydrogen, methyl, ethyl, isopropyl, n-butyl, isobutyl, 2-hydroxyethyl, 3-carboxypropyl, 4-aminobutyl, mercaptomethyl, amidomethyl, hydroxymethyl, methylthioethyl, phenyl, benzyl, hydroxybenzyl, 2-indolylmethyl, 3-inddylmethyl; or $R^2$ and $R^3$, taken together with the nitrogen and carbon to which they are attached, represent 2-pyrrolidyl;

and the non-toxic pharmacologically acceptable salts thereof.

The above compounds (I) and their salts exhibit a strong anthelmintic effect. Also surprisingly, the compounds of this invention (I) exhibit a better therapeutic index than the N'-phenyl-N,N-dimethylacetamidines known from German Offenlegungsschriften (German Published Specification) 2,029,298 and 2,029,299. A smaller amount of the instant compounds (I) can be used compared to the prior art compounds to obtain the same or better results in the treatment of helminthiases, thus reducing the danger of a toxic overdosage.

The products (I) of this invention are obtained by several methods.

a. One such method consists of treating an amino protected acid of the formula:

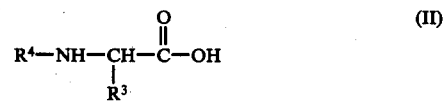

in which $R^4$ is an amino-protecting group and $R^3$ is as defined above with N'-(4-aminophenyl)-N,N-dimethylacetamidine, in the presence of a dehydrating agent, and, preferably, also in the presence of a hydroxy compound, and the protective group $R^4$ is then split off to produce a compound of the invention in which at least one of $R^1$ and $R^2$ is hydrogen.

b. An alternative method provides for the reaction of a carbonyl-activated amino-protected acid of the formula:

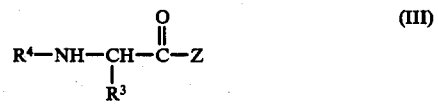

in which $R^3$ and $R^4$ are as defined above and Z is a carbonyl-activating group, with N'-(4-aminophenyl)-N,N-dimethylacetamidine followed by the splitting off of the protective group $R^4$ to produce a compound of the invention in which at least one of $R^1$ and $R^2$ is hydrogen.

c. Another method for preparing the instant products (I) consists in treating an N'-(haloacylaminophenyl)acetamidine of the formula:

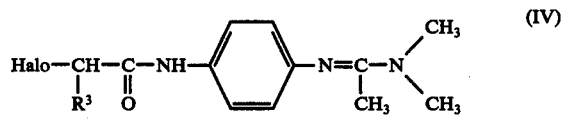

in which $R^3$ is as defined above, with an amine of the formula:

in which $R^1$ and $R^2$ are as defined above, optionally in the presence of a solvent and optionally in the presence of an acid-binding agent. The radical halo in formula (IV) is preferably chloro or bromo.

Hereinafter the foregoing methods shall be identified as Process Variants (a), (b) and (c), respectively.

In principle, in Process Variant (a) the amino-protecting radical $R^4$ may be any amino-protecting radical as, for example, those conventionally used in peptide chemistry. The following are typical of the protecting groups commonly and preferably used: benzyloxycarbonyl, tert.-butoxycarbonyl, p.-tosyl, phthalyl and trifluoroacetyl.

Also, the following are illustrative of amino-acids in which the amino moiety therein is protected by benzyloxycarbonyl or tert.-butoxycarbonyl (corresponding to R⁴ in formula III). Z-L-alanine, Z-D-alanine, Z-L-α-amino-n-butyric acid, Z-α-aminoisobutyric acid, Z-L-isoleucine, Z-D-isoleucine, Z-L-valine, Z-D-valine, Z-DL-phenylglycine, Z-D-phenylglycine, Z-DL-leucine, Z-D-phenylalanine, Z-L-phenylalanine, Z-L-proline, Z-DL-histidine, Z-L-histidine, Z-D-methionine, Z-L-methionine, Z-L-tryptophane, Z-DL-tryptophane, Z-glycine, tBu-L-alanine, tBu-glycine, tBu-L-phenylalanine, tBu-L-leucine, tBu-tryptophane and tBu-DL-methionine.

Also, the dehydrating agents customarily used in peptide chemistry can be employed in Process Variant (a). One preferred dehydrating agent is dicyclohexylcarbodimide.

In Process Variant (a), the protected amino-acid II is preferably reacted with N'-(4-aminophenyl)-N,N-dimethylacetamidine in the presence of an hydroxyl compound. Preferred examples of such hydroxyl compounds are N-hydroxysuccinimide, 1-hydroxybenzotriazole, and 3-hydroxy-4-oxo-3,4-dihydro-1,2,3-benzotriazine.

The amino-protective group R⁴ is split off in accordance with the methods commonly employed in peptide chemistry. Thus, for example, the carbobenzoxy radical can be split off by hydrogenation or by means of hydrogen bromide/glacial acetic acid or with sodium in liquid ammonia. Likewise, tert.-butoxycarbonyl radical can readily be split off with HBr/glacial acetic acid or with anhydrous trifluoroacetic acid.

Also, in conducting the process in accordance with Process Variant (a), 0.1 mol of the compound II is preferably reacted with 0.1 mol of N'-(4-aminophenyl)-N,N-dimethylacetamidine.

The carbonyl-activating radical Z in the formula III may, in principle, be any one of the carbonyl-activating groups conventionally used in peptide synthesis. Preferred among these are the halo- moieties, especially chloro and bromo, the azido group, the imidazolide group or one of the following:

-continued

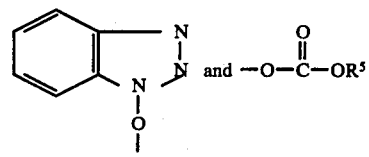 and $-O-\overset{O}{\underset{\|}{C}}-OR^5$ in which R⁵ is an alkyl group, preferably of 1 to 5 carbon atoms as, for example, the methyl, ethyl, n.-propyl, i.-propyl, n.-butyl, i.-butyl and t.-butyl.

Process Variant (b) is preferably carried out in the presence of an acid-binding agent. As acid-binding agent, any inorganic or organic base may be used; the following may be mentioned as examples:

$NaOH$, $KOH$, $NaHCO_3$, $K_2CO_3$, $N(C_2H_5)_3$ and

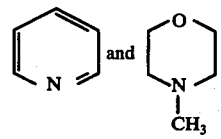

Also, in carrying out the process in accordance with Process Variant (b), 0.1 mol of the carbonyl-activated amino-protected amino acid III is generally reacted with 0.1 mol of N'-(4-aminophenyl)-N,N-dimethylacetamidine at −10° to 30° C, preferably at 0° to 10° C. The amino-protective group R⁴ is preferably split off by pouring the reaction mixture into trifluoroacetic acid or into an HBr/glacial acetic acid mixture, while cooling thoroughly.

If, in Process Variant (a), for example, N-(carbobenzoxy)glycine and N'-(4-aminophenyl)-N,N-dimethylacetamidine are used as starting compounds, the reaction can be represented by the following equation:

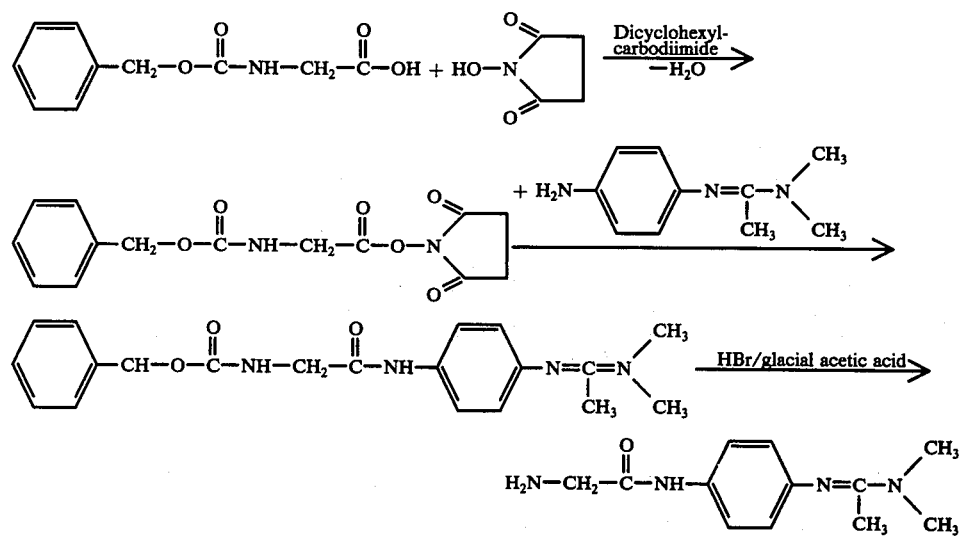

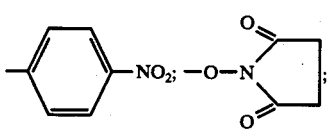

Also, in Process Variant (b), if N-carbobenzoxyglycine, chloroformic acid ester and N'-(4-aminophenyl)-N,N-dimethylacetamidine are used as starting compounds, the course of the reaction can be illustrated by the following equation:

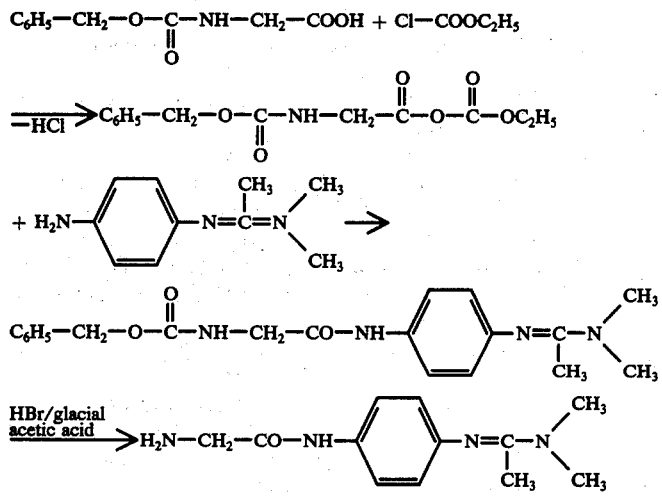

In carrying out the Process Variant (c), 0.1 mol of the compound V is preferably reacted with 0.1 mol of the N'-(haloacylaminophenyl)-acetamidine at room temperature in a polar organic solvent, preferably a liquid aliphatic alcohol, for example methanol or ethanol, and the mixture is then heated to a higher temperature, preferably up to the boiling point of the lower aliphatic alcohol.

If, for example, N'-(4-chloroacetylaminophenyl)-N,N-dimethylacetamidine and diethylamine are used in Process Variant (c) as starting compounds, the course of the reaction can be illustrated by the following equation:

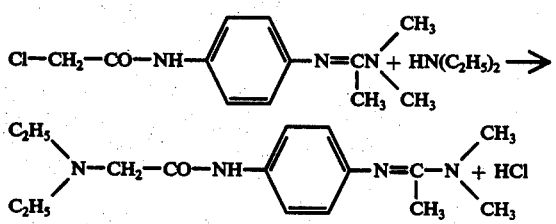

The compounds of the formulae II, III, IV or V which are used as starting compounds in the process of this invention are known or can be prepared by methods which are well known in the art. For example, compounds of the formula IV can be prepared by reacting compounds of the formula:

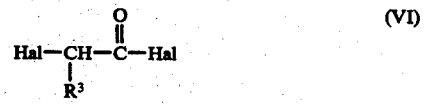

(VI)

in which $R^3$ is as defined above and "Hal" is a halogen atom, especially chlorine or bromine, with N'-(4-aminophenyl)-N,N-dimethylacetamidine, optionally in the presence of a solvent and optionally in the presence of an acid-binding agent.

The three Process Variants (a), (b) and (c) can be carried out in suitable solvents; preferred solvents include all organic solvents that are inert to the reactions. These preferred solvents include hydrocarbons such as benzene, benzine and toluene, ethers such as diethyl ether, dioxane and tetrahydrofuran, halogenated hydrocarbons such as methylene chloride and chloroform and alcohols such as methanol, ethanol and isopropanol, dimethylformamide, dimethylsulfoxide.

The reaction temperatures in Process Variants (a), (b) and (c) can be varied within a wide range. In general, however, temperatures between about 0° and 100° C are commonly used. Also, the reaction of Process Variants (a), (b) and (c) is generally conducted at atmospheric pressure.

The N'-(aminoacylaminophenyl)acetamidines of the formula I and their salts may be selectively prepared and interconverted in any manner; customary methods for the selective preparation and interconversion of free organic bases and their salts may be used. The preferred salts according to the present invention are those that are pharmaceutically acceptable, and may be formed with inorganic or organic acids. Examples of preferred salts are the hydrohalic acid salts (especially the hydrochlorides), naphthalene-disulfonates, methanesulfonates, pamoates (i.e. methylene-bis-(2-hydroxy-(3)-naphthoates), sulfates, phosphates, nitrates and acetates.

It can be seen from the formula I that the compounds of the invention are α-amino acid derivatives containing an assymmetric carbon atom and this invention extends to the D- and L-forms of these compounds as well as to the racemic forms. Therefore, any disclosure herein, unless otherwise expressly stated, is equally applicable to the D-, L-, and DL-form of the compounds. These forms may be selectively prepared, separated, and interconverted in the usual ways known in the art.

The following are illustrative of the instant products (I) and are intended to include the non-toxic pharmacologically acceptable salts thereof:

N,N-dimethyl-N'-(4-L-valylaminophenyl)-acetamidine,
N,N-dimethyl-N'-(4-D-valyl-aminophenyl)-acetamidine,
N,N-dimethyl-N'-(4-DL-valyl-aminophenyl)-acetamidine,
N,N-dimethyl-N'-(4-L-tyrosyl-aminophenyl)-acetamidine,
N,N-dimethyl-N'-(4-DL-tyrosyl-aminophenyl)-acetamidine,
N,N-dimethyl-N'-(4-L-tryptophyl-aminophenyl)-acetamidine,
N,N-dimethyl-N'-(4-DL-tryptophyl-aminophenyl)-acetamidine, N,N-dimethyl-N'-(4-L-threonyl-aminophenyl)-acetamidine,
N,N-dimethyl-N'-(4-DL-threonyl-aminophenyl)-acetamidine,
N,N-dimethyl-N'-(4-L-seryl-aminophenyl)-acetamidine,
N,N-dimethyl-N'-(4-D-seryl-aminophenyl)-acetamidine,
N,N-dimethyl-N'-(4-DL-seryl-aminophenyl)-acetamidine,
N,N-dimethyl-N'-(4-sarcosyl-aminophenyl)-acetamidine,
N,N-dimethyl-N'-(4-L-prolyl-aminophenyl)-acetamidine,
N,N-dimethyl-N'-(4-L-phenyl-alanyl-aminophenyl)-acetamidine,
N,N-dimethyl-N'-(4-D-phenyl-alanyl-aminophenyl)-acetamidine,
N,N-dimethyl-N'-(4-DL-phenylalanyl-aminophenyl)-acetamidine,
N,N-dimethyl-N'-(4-L-methionyl-aminophenyl)-acetamidine,
N,N-dimethyl-N'-(4-DL-methionyl-aminophenyl)-acetamidine,
N,N-dimethyl-N'-(4-L-leucyl-aminophenyl)-acetamidine,
N,N-dimethyl-N'-(4-D-leucyl-aminophenyl)-acetamidine,
N,N-dimethyl-N'-(4-DL-leucyl-aminophenyl)-acetamidine,
N,N-dimethyl-N'-(4-L-isoleucyl-aminophenyl)-acetamidine,
N,N-dimethyl-N'-(4-DL-isoleucyl-aminophenyl)-acetamidine,
N,N-dimethyl-N'-(4-L-histidyl-aminophenyl)-acetamidine,
N,N-dimethyl-N'-(4-DL-histidyl-aminophenyl)-acetamidine,
N,N-dimethyl-N'-(4-glycyl-aminophenyl)-acetamidine,
N,N-dimethyl-N'-(4-L-phenylglycyl-aminophenyl)-acetamidine,
N,N-dimethyl-N'-(4-D-phenylglycyl-aminophenyl)-acetamidine,
N,N-dimethyl-N'-(4-DL-phenylglycyl-aminophenyl)-acetamidine,
N,N-dimethyl-N'-(4-L-lysyl-aminophenyl)-acetamidine,
N,N-dimethyl-N'-(4-DL-lysyl-aminophenyl)-acetamidine,
N,N-dimethyl-N'-(4-L-glutamyl-aminophenyl)-acetamidine,
N,N-dimethyl-N'-(4-DL-glutamyl-aminophenyl)-acetamidine,
N,N-dimethyl-N'-(4-L-asparagyl-aminophenyl)-acetamidine,
N,N-dimethyl-N'-(4-DL-asparagyl-aminophenyl)-acetamidine,
N,N-dimethyl-N'-(4-L-alanyl-aminophenyl)-acetamidine,
N,N-dimethyl-N'-(4-D-alanyl-aminophenyl)-acetamidine,
N,N-dimethyl-N'-(4-DL-alanyl-aminophenyl)-acetamidine,
N,N-dimethyl-N'-(4-L-α-amino-n-butyryl-aminophenyl)-acetamidine,
N,N-dimethyl-N'-(4-DL-α-amino-n-butyryl-aminophenyl)-acetamidine,
N,N-dimethyl-N'-(4-α-aminoisobutyryl-aminophenyl)-acetamidine,
N,N-dimethyl-N'-(4-L-cysteinyl-aminophenyl)-acetamidine and
N,N-dimethyl-N'-(4-D-cysteinyl-aminophenyl)-acetamidine.

As stated above, the compounds of the invention are useful as anthelmintics. In particular, they show, for example, a surprisingly good and broad action against the following nematodes and cestodes:
1. hookworms (for example *Ancylostoma caninum, Uncinaria stenocephala,* and *Bunostomum trigonocephalum*);
2. trichostrongylidae (for example *Nippostrongylus muris* and *Nematospiroides dubius*);
3. strongylidae (for example *Oesophagostomum columbianum*);
4. rhabditidae (for example *Strongyloides ratti*);
5. mawworms (for example *Toxocara canis, Toxascaris leonina* and *Ascaris suum*);
6. threadworms (for example *Aspiculuris tetraptera*);
7. heterakides (for example *Heterakis spumosa*);
8. filariae (for example *Litomosoides carinii* and *Dipetalonema witei*); and
9. cyclophyllidae (for example *Taenia hydatigena, T. pisiformis, Hymenolepis nana, H. diminuta, H. microstoma, Echinococcus multiloculoris* and *E. granulosus*).

The action was tested in animal experiments after oral and parenteral administration to test animals heavily infected with parasites. The dosages used were tolerated very well by the test animals.

The anthelmintic action of some of the active compounds of the invention is illustrated below in Examples A, B and C.

EXAMPLE A

Hookworm test/dog

Dogs experimentally infected with *Uncinaria stenocephala* or *Ancylostoma caninum* were treated after the end of the pre-patency period of the parasites.

The amount of active compound was administered orally as pure active compound in gelatine capsules.

The degree of effect was determined by counting the worms expelled after the treatment and the worms remaining in the test animal, after dissection, and calculating the percentage of the worms expelled.

Table 1 in each case lists the minimum dosage which reduces the worm infection of the test animals by more than 90%. The dosage is quoted in mg of active compound per kg of body weight.

EXAMPLE B

Mawworm test/dog or rat

The amount of active compound was administered orally, as pure active compound in gelatine capsules, to dogs naturally or experimentally infected with *Toxocara canis*.

The degree of effect is determined by counting the worms expelled after the treatment and the worms remaining in the test animal, after dissection, and calculating the percentage of the worms expelled.

Rate experimentally infected with *Ascaris suum* were treated 1 to 3 days after infection. The amount of active compound was administered orally as an aqueous suspension.

The degree of effect of the preparation is determined by counting, after dissection, the worms remaining in the test animal in comparison to untreated control animals and calculating the percentage effect therefrom.

EXAMPLE C

Hymenolepis nana/mouse

Mice experimentally infected with *Hymenolepis nana* were treated after the end of the pre-patency period of the parasites. The amount of active compound was administered orally as an aqueous suspension.

The degree of effect on the preparation is determined by counting, after dissection, the worms remaining in the test animal in comparison to untreated control animals and calculating the percentage effect therefrom.

single dose. A single dose preferably contains an amount sufficient to produce the desired therapeutic effect upon administration at one application of one or more dosage units according to a predetermined dosage regimen, usually a whole, half, third or quarter of the daily dosage administered once, twice, three or four times a day. Other therapeutic agents can also be present.

Although the dosage and dosage regimen must in each case be carefully adjusted, utilizing sound professional judgment and considering the age, weight and condition of the recipient, the route of administration and the nature and gravity of the illness, it is generally advantageous to administer amounts of from about 1 to 100 mg of the compound (I) per kg of body weight per Table 1

$$R-NH-\langle\bigcirc\rangle-N-C=N\begin{array}{c}CH_3\\\diagdown\\CH_3\end{array}CH_3$$

This table lists in each case the lowest dosages of active compound (mg/kg, administered orally) which reduced the worm infection of the test animals by more than 90%.
Toleration means maximum dose (mg/kg) which is survived by the test animal on a single peroral administration.

| R | | Toleration (mouse) | Ascaris larvae (rat) | Hymenolepis nana (mouse) | Ancylostoma caninum (dog) | Uncinaria (dog) | Toxocara (dog) |
|---|---|---|---|---|---|---|---|
| H— | (comparison preparation) | 100 | 25 | 100 | 5 | 10 | 2.5 |
| $H_3C-O-CH_2-\overset{O}{\underset{\parallel}{C}}-$ | (comparison preparation) | 500 | 500 | — | 25 | 25 | 25 |
| $D-Ph-\underset{NH_2}{\overset{\mid}{CH}}-\overset{O}{\underset{\parallel}{C}}-$ | | 500 | 10 | — | — | — | — |
| $L-Ph-CH_2-\underset{NH_2}{\overset{\mid}{CH}}-\overset{O}{\underset{\parallel}{C}}-$ | | 1,000 | 25 | 250 | 5 | 5 | 10 |
| $L-\underset{CH_3}{\overset{CH_3}{\diagdown}}CH-CH_2-\underset{NH_2}{\overset{\mid}{CH}}-\overset{O}{\underset{\parallel}{C}}-$ | | 500 | 25 | 50 | 2.5 | 5 | — |
| $H_2N-CH_2-\overset{O}{\underset{\parallel}{C}}-$ | | 500 | 100 | 10 | 5 | 5 | 5 |
| $L-\underset{CH_3}{\overset{CH_3}{\diagdown}}CH-\underset{NH_2}{\overset{\mid}{CH}}-\overset{O}{\underset{\parallel}{C}}-$ | | 1,000 | 50 | 10 | 2.5 | 10 | — |
| $L-CH_3-\underset{}{\overset{NH_2}{\overset{\mid}{HC}}}-\overset{O}{\underset{\parallel}{C}}-$ | | 1,000 | 25 | — | 10 | 5 | — |

The compounds (I) of this invention can be utilized as the active ingredient in anthelmintic compositions having utility in human and veterinary medicine. These compositions contain a major or minor amount of at least one compound (I) of this invention as, for example, from about 99.5% to 0.1%, preferably 95% to 0.5%, and most preferably from about 0.5% to 90% of the compound (I) in combination with a pharmaceutically acceptable non-toxic inert diluent or carrier. The diluent or carrier comprises one or more solid, semi-solid or liquid medium, filler or formulation adjuvant which is non-toxic, inert and pharmaceutically acceptable. Also, the instant compositions are preferably in dosage units form; i.e., in physically discrete units containing a predetermined amount of the drug corresponding to a fraction or multiple of the dose which is calculated to produce the desired therapeutic response. The dosage units can contain one, two, three, four or more single doses or, alternatively, one-half, third or fourth of a day. In some instances a sufficient therapeutic effect can be obtained at a lower dose while in others, a larger dose will be required.

Oral administration can be effected utilizing solid and liquid dosage unit forms such as powders, tablets, dragees, capsules, granulates, suspensions, solutions, ampoules or suppositories, and the like.

Powders are prepared by comminuting the compound to a suitable fine size and mixing with a similarly comminuted pharmaceutical carrier such as an edible carbohydrate as for example starch, lactose, sucrose, glucose or mannitol. Sweetening, flavoring, preservative, dispersing and coloring agents can also be present.

Capsules are made by preparing a powder mixture as described above and filling formed gelatin sheaths. Glidants and lubricants such as colloidal silica, talc, magnesium stearate, calcium stearate or solid polyethylene glycol can be added to the powder mixture before the filling operation. A disintegrating or solubilizing agent such as agar-agar, calcium carbonate or sodium carbonate can also be added to improve the availability of the medicament when the capsule is ingested.

Tablets are formulated for example by preparing a powder mixture, granulating or slugging, adding a lubricant and disintegrant and pressing into tablets. A powder mixture is prepared by mixing the compound, suitably comminuted, with a diluent or base as described above, and optionally with a binder such as carboxymethyl, cellulose, an alginate, gelatin, or polyvinyl pyrrolidone, a solution retardant such as paraffin, a resorption accelerator such as a quaternary salt and/or an absorption agent such as bentonite, kaolin or dicalcium phosphate. The powder mixture can be granulated by wetting with a binder such as syrup, starch paste, acacia mucilage or solutions of cellulosic or polymeric materials and forcing through a screen. As an alternative to granulating, the powder mixture can be run through the tablet machine and the resulting imperfectly formed slugs broken into granules. The granules can be lubricated to prevent sticking to the tablet forming dies by means of the addition of stearic acid, a stearate salt, talc or mineral oil. The lubricated mixture is then compressed into tablets. The medicaments can also be combined with free flowing inert carriers and compressed into tablets directly without going through the granulating or slugging steps. A clear or opaque protective coating consisting of a sealing coat of shellac, a coating of sugar or polymeric material and a polish coating of wax can be provided. Dyestuffs can be added to these coatings to distinguish different unit dosages.

The diluents to be used in pharmaceutical compositions for formulation into tablets, dragees, capsules and pills include the following:

(a) fillers and extenders: starch, sugars, mannitol, and silicic acid; (b) binding agents: carboxymethyl cellulose and other cellulose derivatives, alginates, gelatine and polyvinyl pyrrolidone; (c) moisturizing agents: glycerol; (d) disintegrating agents: agar-agar, calcium carbonate and sodium bicarbonate; (d) agents for retarding dissolution: paraffin; (f) resorption accelerators: quaternary ammonium compounds; (g) surface active agents: cetyl alcohol and glycerol monostearate; (h) adsorptive carriers: kaolin and bentonite; (i) lubricants: talc, calcium and magnesium stearate and solid polyethylene glycols.

The tablets, dragees, capsules and pills formed from the pharmaceutical compositions of the invention can have the customary coatings, envelopes and protective matrices, which may contain opacifiers. They can be constituted as a timed release or sustained release formulation so that they release only the active ingredient or, preferably, release the active ingredient in a particular part of the intestinal tract, possibly over a period of time. Thus, for example, the coatings, envelopes and protective matrices may be made, of polymeric substances or waxes.

Oral fluids such as solutions, syrups and elixirs can be prepared in dosage unit form so that a given quantity contains a predetermined amount of the compound. Syrups can be prepared by dissolving the compound in a suitably flavored aqueous sucrose solution while elixirs are prepared through the use of a non-toxic alcoholic vehicle. Suspensions can be formulated by dispersing the compound in a non-toxic vehicle. Solubilizers and emulsifiers such as ethoxylated isostearyl alcohols and polyoxyethylene sorbitol esters, preservatives, flavor additives such as peppermint oil or saccharin, and the like can also be added.

Where appropriate, dosage unit formulations for oral administration can be microencapsulated. The formulation can also be prepared to prolong or sustain the release as for example by coating or embedding particulate material in polymers, wax or the like.

Parenteral administration can be effected utilizing liquid dosage unit forms such as sterile solutions and suspensions intended for subcutaneous, intramuscular or intravenous injection. These are prepared by suspending or dissolving a measured amount of the compound in a nontoxic liquid vehicle suitable for injection such as an aqueous or oleaginous medium and sterilizing the suspension or solution. Alternatively, a measured amount of the compound is placed in a vial and the vial and its contents are sterilized and sealed. An accompanying vial or vehicle can be provided for mixing prior to administration. Nontoxic salts and salt solutions can be added to render the injection isotonic. Stabilizers, preservatives and emulsifiers can also be added.

Rectal administration can be effected utilizing suppositories in which the compound is admixed with low melting water soluble or insoluble solids such as polyethylene glycol, cocoa butter, higher esters as for example myristyl palmitate, or mixtures thereof.

Topical administration can be effected utilizing solid dosage unit forms such as powders or liquid or semiliquid dosage unit forms such as solutions, suspensions, ointments, pastes, creams and gels. The powders are formulated utilizing such carriers as talc, bentonite, silicic acid, polyamide powder, animal and vegetable fats, waxes, paraffins, starch, tragacanth, cellulose derivatives, polyethylene glycols, silicones, talc and zinc oxide or mixtures of these substances. Liquid and semiliquid formulations can utilize such carriers, in addition to those described above, as polyethylene glycol, vegetable and mineral oils, alcohols such as isopropanol and the like. Other excipients such as emulsifiers, preservatives, colorants, perfumes and the like can also be present.

Formulations can also be administered as an aerosol, utilizing the usual propellants such as the chlorofluorohydrocarbons. The pharmaceutical compositions which are sprays can also contain the usual diluents, e.g. lactose, talc, silicic acid, aluminium hydroxide, calcium silicate, and polyamide powder or mixtures of these substances. Aerosol sprays can, for example, contain the usual propellants, e.g. chlorofluorohydrocarbons.

The pharmaceutical compositions which are solutions and emulsions can, for example, contain the customary diluents (with, of course, the above-mentioned exclusion of solvents having a molecular weight below 200 except in the presence of a surface-active agent), such as solvents, dissolving agents and emulsifiers; specific examples of such diluents are water, ethyl alcohol, isopropyl alcohol, ethyl carbonate, ethyl acetate, benzyl alcohol, benzyl benzoate, propylene glycol, 1,3-butylene glycol, dimethylformamide, oils (for example ground nut oil), glycerol, tetrahydrofurfuryl alcohol, polyethylene glycols and fatty acid esters of sorbitol or mixtures thereof.

The pharmaceutical compositions which are suspensions can contain the usual diluents, such as liquid diluents, e.g. water, ethyl alcohol, propylene glycol, surface-active agents (e.g. ethoxylated isostearyl alcohols, polyoxyethylene sorbite and sorbitane esters), microcrystalline cellulose, aluminium metahydroxide, bentonite, agar-agar and tragacanth or mixtures thereof.

All the pharmaceutical compositions according to the invention can also contain coloring agents and preservatives as well as perfumes and flavoring additions (e.g. peppermint oil and eucalyptus oil) and sweetening agents (e.g. saccharin).

The following examples describe by way of illustration the production, by the process of the invention, of a number of compounds of the invention.

EXAMPLE 1

N,N-Dimethyl-N'-(4-L-Leucylaminophenyl)-Acetamidine

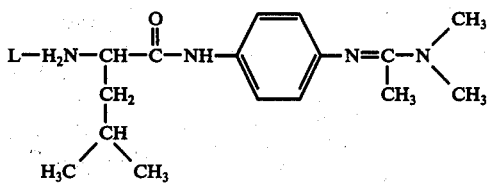

A solution of 17.7 g (0.1 mol) of N'-(4-aminophenyl)-N,N-dimethylacetamidine in 100 ml of absolute tetrahydrofuran was added dropwise to a solution of 32.8 g (0.1 mol) of N-(t-butoxycarbonyl)-L-leucine-N-hydroxysuccinimide ester in 150 ml of absolute tetrahydrofuran at 0° to 5° C. The mixture was then stirred overnight at room temperature and the solvent was then stripped off in vacuo. The residue was dissolved in 250 ml of trifluoroacetic acid, with intense cooling. The solution was stirred for ½ hour at room temperature and then concentrated on a rotary evaporator, the bath temperature being about 35° C. The residue was dissolved in a little water and rendered alkaline with concentrated sodium hydroxide solution, while cooling intensely. The mixture was then repeatedly extracted with toluene. The organic extracts were dried and concentrated in vacuo. The residue was recrystallized from ether. 14.3 g (44% of theory) of N,N-dimethyl-N'-(4-L-leucylaminophenyl)-acetamidine of melting point 106° to 107° C were obtained.

$C_{16}H_{26}N_4O$; molecular weight 290.4 — Calculated: C = 66.2, H = 9.0, N = 19.3 wt %. Found: C = 66.6, H = 9.1, N = 19.1 wt %.

EXAMPLE 2

N,N-Dimethyl-N'-(4-D-Phenylglycylaminophenyl) Acetamidine

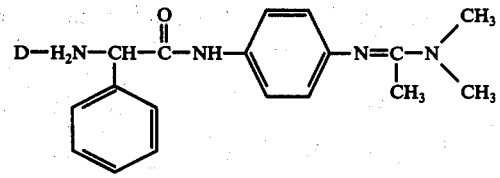

7 g (0.039 mol) of N'-(4-aminophenyl)-N,N-dimethylacetamidine were added, while stirring, to a solution of 15 g (0.039 mol) of N-(carbobenzoxy)-D-phenylglycin-N-hydroxysuccinimide ester in 250 ml of absolute tetrahydrofuran. The mixture was stirred overnight at room temperature. It was then concentrated in vacuo, rendered alkaline with dilute sodium hydroxide solution at 0° to 5° C and repeatedly extracted with chloroform. The organic extracts were dried and concentrated. The residue was dissolved in a small amount of tetrahydrofuran and reprecipitated by the addition of ether. There was thus obtained 9.0 g of product which was slowly introduced into 100 ml of HBr/glacial acetic acid with cooling. The mixture was stirred for 2 hours at room temperature and then stirred into 700 ml of dry ether. A crystalline precipitate formed and this product was filtered off, washed with ether and then dissolved in water. The aqueous solution was then rendered alkaline, while cooling, and the solution repeatedly extracted with chloroform. The organic extracts were dried over $Na_2SO_4$ and concentrated in vacuo, and the residue recrystallized from a mixture of tetrahydrofuran and ether. There was thus obtained 4.4 g (36% of theory) of N,N-dimethyl-N'-(4-D-phenylglycylaminophenyl)acetamidine, melting point 141°–143° C.

$C_{18}H_{22}N_4O$: Molecular weight 310.4 — Calculated: C = 69.7, H = 7.0, N = 18.1 wt %. Found: C = 69.5, H = 7.0, N = 18.1 wt %.

The following compounds were prepared by following the procedure of Example 2 upon substituting for the N-hydroxysuccinimide ester reactants therein the appropriate starting materials:

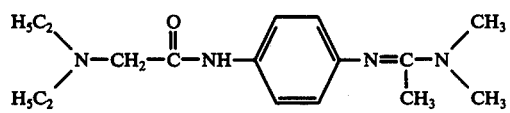

| $R^3$ | Configuration | Yield | Melting Point |
|---|---|---|---|
| —Ph | D,L | 35% | 134 – 136° C |
| —H | — | 65% | 142 – 145° C |
| —$CH_3$ | L | 63% | Dihydrochloride: 220 – 223° C |
| Ph—$CH_2$— | L | 60% | 81 – 85° C |
| $H_3C$\\CH—/$H_3C$ | L | 42% | Dihydrochloride: 190 – 195° C |

The starting materials employed in preparing the products of claims 10, 11, 12, 13, 14 are:

N-(carbobenzoxy)-DL-phenylglycine-N-hydroxysuccinimide ester

N-(carbonbenzoxy)-glycine-N-hydroxysuccineimide ester

N-(carbobenzoxy)-L-alanine-N-hydroxysuccinimide ester

N-(carbobenzoxy)-L-phenylalanine-N-hydroxysuccinimide ester

N-(carbobenzoxy)-L-valine-N-hydroxysuccinimide ester

EXAMPLE 3

N'-(4-Diethylaminoacetylaminophenyl)-N,N-Dimethylacetamidine

Step A: N'-(4-Chloroacetylaminophenyl)-N,N-Dimethylacetamidine Hydrochloride

N'-(4-Chloroacetylaminophenyl)-N,N-dimethylacetamidine hydrochloride, used as the starting material in Step B of this example, is obtained by the acylation of 74.5 g of N'-(4-aminophenyl)-N,N-dimethylacetamidine with 54.7 g of chloroacetyl chloride in tetrahydrofuran to afford 104.7 g of the product. Upon recrystallization from alcohol the N'-(4-chloroacetylaminophenyl)-N,N-dimethylacetamidine hydrochloride has a melting point of 246°–247° C.

Step B: N'-(4-Diethylaminoacetylaminophenyl)-N,N-Dimethylacetamidine 1 g of potassium iodide is added to a solution of 23.2 g of N'-(4-chloroacetylaminophenyl)-N,N-dimethylacetamidine hydrochloride in 250 ml of ethanol and 14.6 g of diethylamine are added dropwise at 20° C. The mixture is heated under reflux for 2 hours and evaporated in vacuo, the residue is dissolved in water, sodium hydroxide solution is added and the organic phase is extracted with ether/chloroform. After distilling the organic phase, 7.9 g of N'-(4-diethylaminoacetylaminophenyl)-N,N-dimethylacetamidine, boiling point$_{0.2}$ 185°–187° C, are obtained. Addition of 1 mol of naphthalenedisulphonic acid to 1 mol of the base gives the naphthalenedisulphonate, melting point >260° C (decomposition) (recrystallized from ethanol/H$_2$O). The naphthalene-disulphonate is best prepared from the crude undistilled base and naphthalenedisulphonic acid. $C_{26}H_{34}N_4O_7S_2$; molecular weight 578.58 — Calculated: C = 53.97, H = 5.92, N = 9.68 wt %. Found: C = 53.7, H = 5.6, N = 9.9 wt %.

The following compounds are prepared in an analogous manner by treating N'-(4-chloroacetylaminophenyl)-N,N-dimethylacetamidine with ammonia or with an appropriate primary or secondary amine. The following equation and accompanying Table illustrate the process of Example 3, Steps A and B and, together with the Table illustrate the starting materials which may be employed in the process and the acetamidine products obtained thereby:

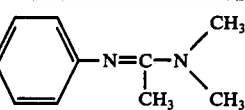

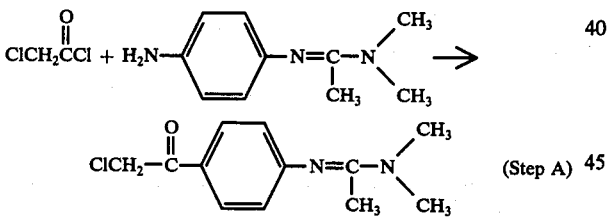

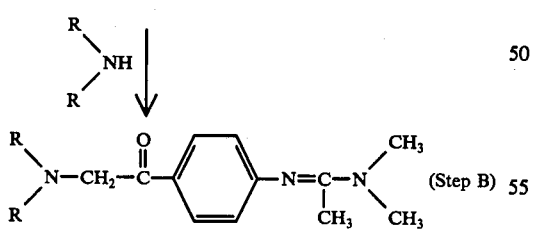

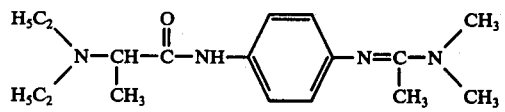

| —NRR | Boiling point (° C/mm Hg) | Naphthalenedisulfonate melting point (° C) |
|---|---|---|
| —HN—CH$_3$ | 210 – 212° C/0.5 | >280° C (decomposition) |
| —HN—C$_2$H$_5$ | | >260° C (decomposition) |
| —HN—C$_4$H$_9$ | | >260° C (decomposition) |
| —N(CH$_3$)$_2$ | | >290° C (decomposition) |

-continued

| —NRR | Boiling point (° C/mm Hg) | Naphthalenedisulfonate melting point (° C) |
|---|---|---|
| —N⟨ ⟩ (piperidine) | | >260° C (decomposition) |
| —N⟨ ⟩O (morpholine) | | >260° C (decomposition) |
| —NH$_2$ | | Base: melting point 142–145° C |

EXAMPLE 4

N'-[4-(α-Diethylaminopropionyl)-aminophenyl]-N,N-Dimethylacetamidine

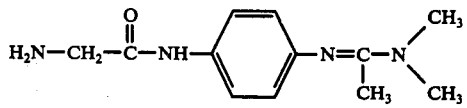

Step A: N'-[4-(α-Bromopropionyl)aminophenyl]-N,N-Dimethylacetamidine Hydrochloride The hydrochloride reactant of Step B in this example (melting point 236°–237° C) is obtained by the reaction of N'-(4-aminophenyl)-N,N-dimethylacetamidine and α-bromopropionyl chloride.

Step B: N'-[4-(α-Diethylaminopropionyl)aminophenyl]-N,N-dimethylacetamidine

Following the procedure described in Example 3, reaction of 27.5 g of N'[4-(α-bromopropionyl)aminophenyl]-N,N-dimethylacetamidine hydrochloride with 40 g of diethylamine gives N'-[4-(α-diethylaminopropionyl)aminophenyl]-N,N-dimethylacetamidine, which is converted, in the crude form, into the naphthalenedisulphonate by means of one equivalent of naphthalenedisulphonic acid. Yield 16 g, melting point >260° C (decomposition) (recrystallized from ethanol/H$_2$O).

Following the procedure of Example 4 but substituting piperidine for the diethylamine reactant there is thus obtained N'-[4-(α-piperidinopropionyl)aminophenyl]-N,N-dimethylacetamidine as the naphthalenedisulphonate.

EXAMPLE 5

N,N-Dimethyl-N'-(4-Glycylaminophenyl)acetamidine 22.8 g (0.21 mol) of chloroformic acid ethyl ester were added dropwise at −15° C to a solution of 41.8 g (0.2 mol) of N-(carbobenzoxy)-glycine and 21.3 g (0.21 mol) of N-methylmorpholine in 250 ml of absolute tetrahydrofuran. The mixture was stirred for 10 minutes at −10° C and was then filtered. A solution of 33.7 g (0.19 mol) of N'-(4-aminophenyl)-N,N-dimethylacetamidine in 100 ml of absolute tetrahydrofuran was added dropwise to the filtrate at −10° C. The mixture was then stirred for 30 minutes at −10° C, 1 hour at 0° C and 2 hours at room temperature. Thereafter, the mixture was concentrated on a rotary evaporator, suspended in sodium hydroxide solution and repeatedly extracted with chloroform. The chloroform phase was dried with $Na_2SO_4$ and concentrated. The residue was recrystallized from benzene-ligroin. 39.2 g of N'-[4-(carbobenzoxy-glycylamino)-phenyl]-N,N-dimethylacetamidine of melting point 133° C were thus obtained and were slowly introduced into 800 ml of HBr/glacial acetic acid, with cooling. The mixture was stirred for 2 hours at room temperature and was then stirred into 2 liters of dry ether. A crystalline precipitate formed and this was filtered off, washed with ether and then dissolved in water. The aqueous solution was rendered alkaline, with cooling, and was repeatedly extracted with chloroform. The organic extracts were dried over $Na_2SO_4$ and concentrated in vacuo. The residue was recrystallized from toluene to afford 22.9 g (51% of theory) of N,N-dimethyl-N'-(4-glycylaminophenyl)acetamidine, melting point 142°–145° C.

$C_{12}H_{18}N_4O$; molecular weight 234.3 — Calculated: C = 61.5, H = 7.7, N = 23.9 wt %. Found: C = 61.2, H = 8.0, N = 23.8 wt %.

What is claimed is:

1. A compound of the formula:

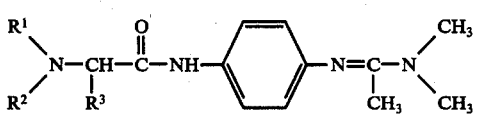

or a pharmaceutically acceptable non-toxic salt thereof wherein
$R^1$ and $R^2$ are the same or different and each is hydrogen or lower alkyl unsubstituted or substituted by lower alkoxy; and
$R^3$ is hydrogen, or lower alkyl unsubstituted or substituted by lower alkoxy.

2. A compound according to claim 1 wherein $R^3$ is hydrogen or lower alkyl.

3. A compound according to claim 1 wherein
$R^1$ and $R^2$ are the same or different and each is hydrogen, or alkyl of 1 to 6 carbon atoms unsubstituted or substituted by alkoxy of 1 to 4 carbon atoms; and
$R^3$ is hydrogen, or alkyl of 1 to 4 carbon atoms unsubstituted or substituted by alkoxy of 1 to 4 carbon atoms.

4. A compound according to claim 1 wherein
$R^1$ and $R^2$ are the same or different and each is hydrogen, or alkyl of 1 to 4 carbon atoms unsubstituted or substituted by alkoxy of 1 or 2 carbon atoms; and
$R^3$ is hydrogen, or alkyl of 1 or 2 carbon atoms unsubstituted or substituted by alkoxy of 1 or 2 carbon atoms.

5. A compound according to claim 1 wherein
$R^1$ and $R^2$ are the same or different and each is hydrogen or alkyl of 1 to 5 carbon atoms; and
$R^3$ is hydrogen, or alkyl of 1 to 5 carbon atoms.

6. A compound according to claim 1 wherein
$R^1$ and $R^2$ are the same or different and each is hydrogen, methyl, ethyl or n-butyl; and
$R^3$ is hydrogen, methyl, ethyl, isopropyl, n-butyl or isobutyl.

7. A compound according to caim 1 wherein
$R^1$ and $R^2$ are the same or different and each is hydrogen, methyl, ethyl, or n-butyl; and
$R^3$ is hydrogen, methyl, isopropyl or n-butyl.

8. A compound according to claim 1 of the formula:

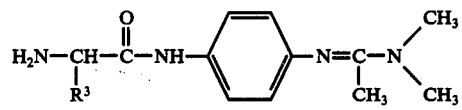

wherein
$R^3$ is hydrogen, methyl, ethyl, isopropyl or isobutyl.

9. The compound according to claim 1 which is:

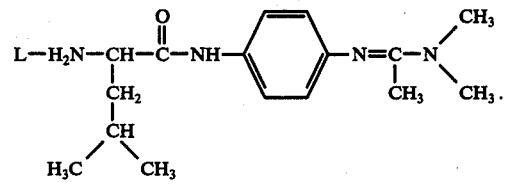

10. The compound according to claim 1 which is:

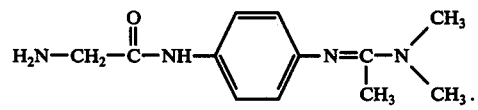

11. The compound according to claim 1 which is:

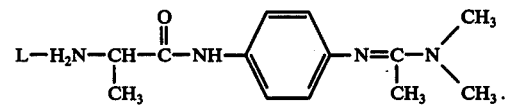

12. The compound according to claim 1 which is:

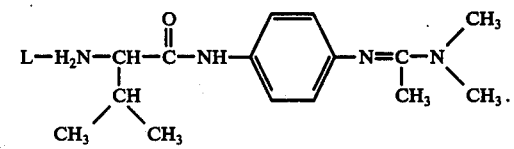

13. The compound according to claim 1 which is:

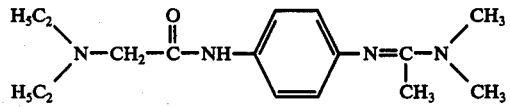

14. The compound according to claim 1 which is:

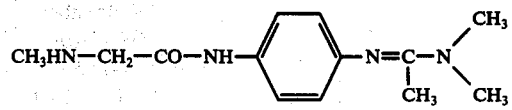

15. The compound according to claim 1 which is:

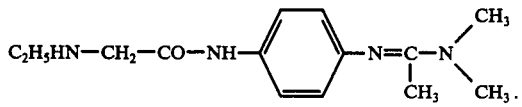

16. The compound according to claim 1 which is:

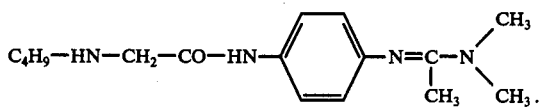

17. The compound according to claim 1 which is:

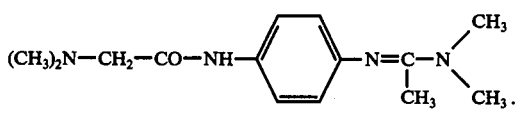

18. The compound according to claim 1 which is:

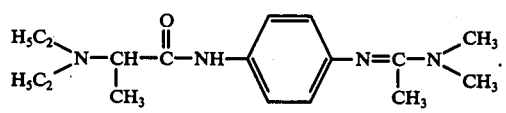

19. The compound according to claim 1 which is:

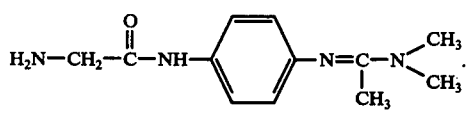

20. An anthelmintic composition useful for treathelminthic infections in humans and animals which comprises an anthlemintically effective amount of a compound of the formula

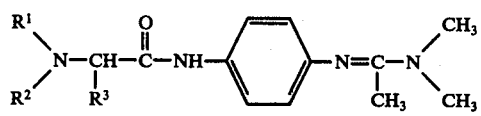

or a pharmaceutically acceptable non-toxic salt thereof wherein
R$^1$ and R$^2$ are the same or different and each is hydrogen, or lower alkyl unsubstituted or substituted by lower alkoxy; and
R$^3$ is hydrogen, or lower alkyl unsubstituted or substituted by lower alkoxy;
in combination with a pharmaceutically acceptable non-toxic inert diluent or carrier.

21. A composition according to claim 20 wherein R$^3$ is hydrogen or lower alkyl.

22. A composition according to claim 20 wherein
R$^1$ and R$^2$ are the same or different and each is hydrogen, or alkyl of 1 to 6 carbon atoms unsubstituted or substituted by alkoxy of 1 to 4 carbon atoms; and
R$^3$ is hydrogen, or alkyl of 1 to 4 carbon atoms unsubstituted or substituted by alkoxy of 1 to 4 carbon atoms.

23. A composition according to claim 20 wherein
R$^1$ and R$^2$ are the same or different and each is hydrogen, or alkyl of 1 to 4 carbon atoms unsubstituted or substituted by alkoxy of 1 or 2 carbon atoms; and
R$^3$ is hydrogen, or alkyl of 1 or 2 carbon atoms unsubstituted or substituted by alkoxy of 1 or 2 carbon atoms.

24. A composition according to claim 20 wherein
R$^1$ and R$^2$ are the same or different and each is hydrogen or alkyl of 1 to 5 carbon atoms; and
R$^3$ is hydrogen, or alkyl of 1 to 5 carbon atoms.

25. A composition according to claim 20 wherein
R$^1$ and R$^2$ are the same or different and each is hydrogen, methyl, ethyl or n-butyl; and
R$^3$ is hydrogen, methyl, ethyl, isopropyl, n-butyl or isobutyl.

26. A composition according to claim 20 wherein
R$^1$ and R$^2$ are the same or different and each is hydrogen, methyl, ethyl, or n-butyl; and
R$^3$ is hydrogen, methyl, isopropyl or n-butyl.

27. A composition according to claim 20 of the formula

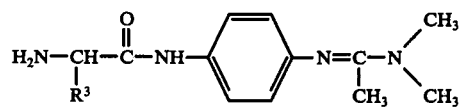

wherein
R$^3$ is hydrogen, methyl, ethyl, isopropyl or isobutyl.

28. A composition according to claim 20 wherein the compound is

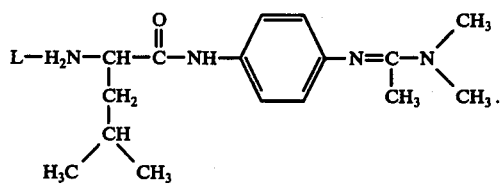

29. A composition according to claim 20 wherein the compound is

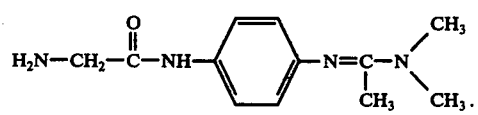

30. A composition according to claim 20 wherein the compound is

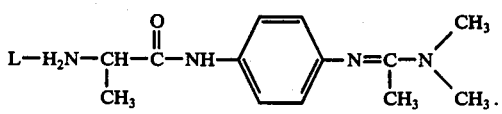

31. A composition according to claim 20 wherein the compound is

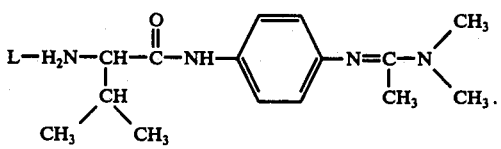

32. A composition according to claim 20 wherein the compound is

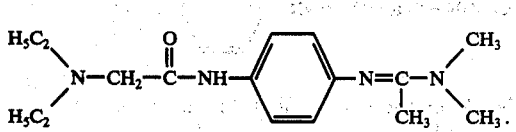

33. A composition according to claim 20 wherein the compound is

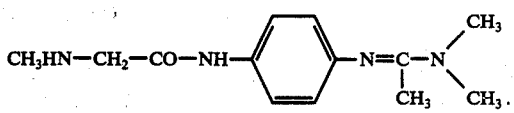

34. A composition according to claim 20 wherein the compound is

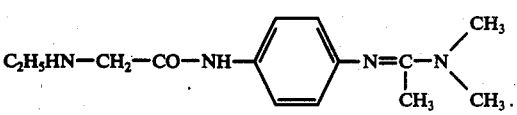

35. A composition according to claim 20 wherein the compound is

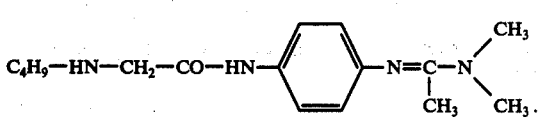

36. A composition according to claim 20 wherein the compound is

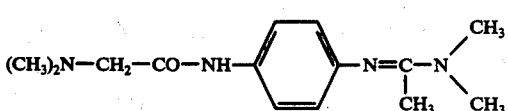

37. A composition according to claim 20 wherein the compound is

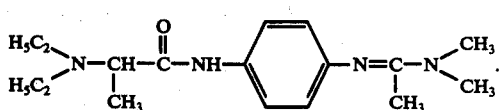

38. A composition according to claim 20 wherein the compound is

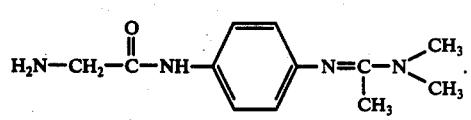

39. A method for treating helminthic infections in humans and animals which comprises administering to a human or animal in need thereof an anthelmintically effective amount of a compound of the formula

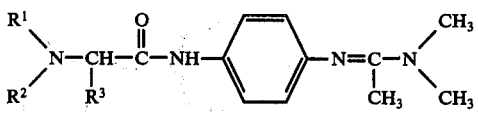

or a pharmaceutically acceptable non-toxic salt thereof wherein $R^1$ and $R^2$ are the same or different and each is hydrogen or lower alkyl unsubstituted or substituted by lower alkoxy; and $R^3$ is hydrogen, or lower alkyl unsubstituted or substituted by lower alkoxy.

40. A method according to claim 39 wherein $R^3$ is hydrogen or lower alkyl.

41. A method according to claim 39 wherein $R^1$ and $R^2$ are the same or different and each is hydrogen, or alkyl of 1 to 6 carbon atoms unsubstituted or substituted by alkoxy of 1 to 4 carbon atoms; and $R^3$ is hydrogen, or alkyl of 1 to 4 carbon atoms unsubstituted or substituted by alkoxy of 1 to 4 carbon atoms.

42. A method according to claim 39 wherein $R^1$ and $R^2$ are the same or different and each is hydrogen, or alkyl of 1 to 4 carbon atoms unsubstituted or substituted by alkoxy of 1 or 2 carbon atoms; and $R^3$ is hydrogen, or alkyl of 1 or 2 carbon atoms unsubstituted or substituted by alkoxy of 1 or 2 carbon atoms.

43. A method according to claim 39 wherein $R^1$ and $R^2$ are the same or different and each is hydrogen or alkyl of 1 to 5 carbon atoms; and $R^3$ is hydrogen, or alkyl of 1 to 5 carbon atoms.

44. A method according to claim 39 wherein $R^1$ and $R^2$ are the same or different and each is hydrogen, methyl, ethyl or n-butyl; and $R^3$ is hydrogen, methyl, ethyl, isopropyl, n-butyl or isobutyl.

45. A method according to claim 39 wherein $R^1$ and $R^2$ are the same or different and each is hydrogen, methyl, ethyl, and n-butyl; and $R^3$ is hydrogen, methyl, isopropyl or n-butyl.

46. A method according to claim 39 of the formula:

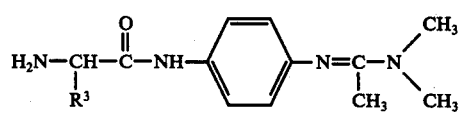

wherein $R^3$ is hydrogen, methyl, ethyl, isopropyl or isobutyl.

47. A composition according to claim 20 in oral administration form.

48. A composition according to claim 20 in parenteral administration form.

49. A composition according to claim 20 in topical application form.

50. A method according to claim 39 wherein the administration is oral.

51. A method according to claim 39 wherein the administration is parenteral.

52. A method according to claim 39 wherein the administration is by topical application.

53. A method according to claim 39 wherein the compound is

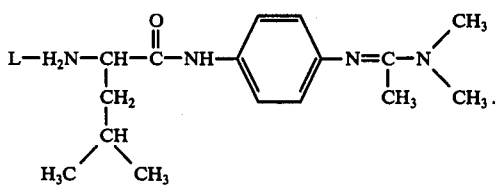

54. A method according to claim 39 wherein the compound is

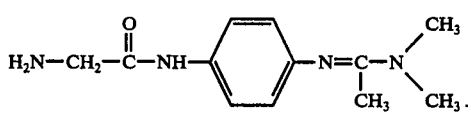

55. A method according to claim 39 wherein the compound is

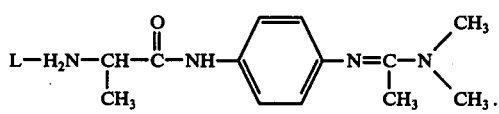

56. A method according to claim 39 wherein the compound is

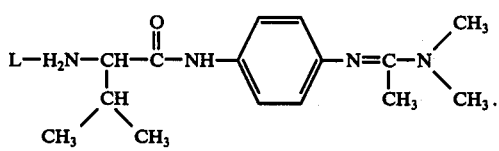

57. A method according to claim 39 wherein the compound is

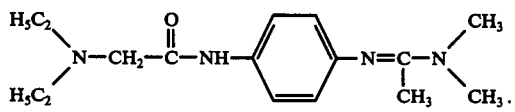

58. A method according to claim 39 wherein the compound is

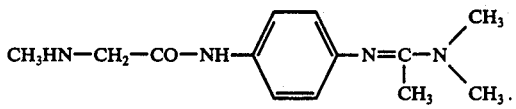

59. A method according to claim 39 wherein the compound is

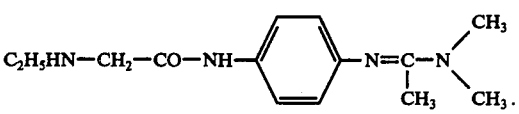

60. A method according to claim 39 wherein the compound is

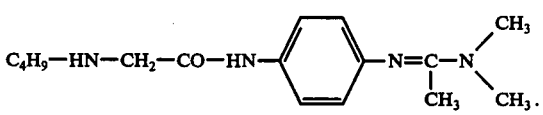

61. A method according to claim 39 wherein the compound is

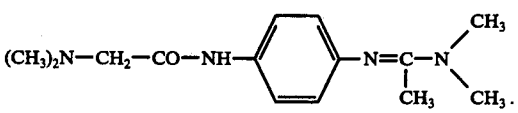

62. A method according to claim 39 wherein the compound is

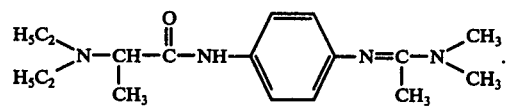

63. A method according to claim 39 wherein the compound is

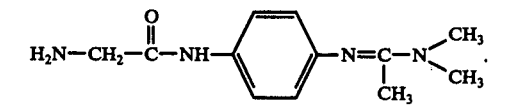

* * * * *